United States Patent [19]

van Gorkom et al.

[11] 4,370,797

[45] Feb. 1, 1983

[54] METHOD OF SEMICONDUCTOR DEVICE FOR GENERATING ELECTRON BEAMS

[75] Inventors: Gerardus G. P. van Gorkom; Arthur M. E. Hoeberechts, both of Eindhoven, Netherlands

[73] Assignee: U.S. Philips Corporation, New York, N.Y.

[21] Appl. No.: 268,209

[22] Filed: May 29, 1981

Related U.S. Application Data

[62] Division of Ser. No. 84,041, Oct. 12, 1979, Pat. No. 4,303,930.

[30] Foreign Application Priority Data

Jul. 13, 1979 [NL] Netherlands .......................... 7905470

[51] Int. Cl.³ .................... H01L 21/223; H01L 21/26
[52] U.S. Cl. ............................... 29/569 R; 29/576 R; 29/580; 29/591; 148/187; 313/303; 313/366
[58] Field of Search .................. 29/569 R, 591, 576 R, 29/580; 148/187, 1.5; 313/303, 366; 352/13, 52, 55

[56] References Cited

U.S. PATENT DOCUMENTS

| | | | |
|---|---|---|---|
| 3,735,210 | 5/1973 | Kalish et al. | 317/234 R |
| 3,894,332 | 7/1975 | Nathanson et al. | 29/580 X |
| 3,909,119 | 9/1975 | Wolley | 357/13 |
| 3,970,487 | 7/1976 | Dahmen et al. | 148/187 X |
| 3,970,887 | 7/1976 | Smith et al. | 331/336 X |
| 4,008,412 | 2/1977 | Yuito et al. | 29/580 X |
| 4,079,402 | 3/1978 | Dunkley et al. | 357/13 |
| 4,095,133 | 6/1978 | Hoeberechts | 313/336 |
| 4,099,998 | 7/1978 | Ferro et al. | 148/187 |
| 4,102,732 | 7/1978 | Kato et al. | 29/580 X |
| 4,259,678 | 3/1981 | Van Gorkom et al. | 357/13 |
| 4,292,642 | 9/1981 | Appels et al. | 357/52 X |

FOREIGN PATENT DOCUMENTS 1303659  1/1973  United Kingdom .

OTHER PUBLICATIONS

"Hot Electron Emission From Shallow p-n Junctions in Silicon", Bartelink et al., Physical Review, vol. 130, No. 3, pp. 972-985, May 1, 1963.

Primary Examiner—G. Ozaki
Attorney, Agent, or Firm—Marc D. Schechter

[57] ABSTRACT

The invention relates to a semiconductor cathode and a camera tube and a display tube, respectively, having such a cathode, based on avalanche breakdown in a p-n junction extending parallel to the surface of the semiconductor body. The released electrons obtain extra energy by means of an accelerating electrode provided on the device. The resulting efficiency increase makes the manufacture of such cathodes in planar silicon technology practical. Since the depletion zone of the p-n junction upon avalanche breakdown does not extend to the surface, the released electrons show a sharp, narrow energy distribution. This makes such cathodes particularly suitable for camera tubes. In addition they find application, for example, in display tubes and flat displays.

5 Claims, 24 Drawing Figures

METHOD OF SEMICONDUCTOR DEVICE FOR GENERATING ELECTRON BEAMS

This is a division of application Ser. No. 084,041, filed Oct. 12, 1979, now U.S. Pat. No. 4,303,930.

BACKGROUND OF THE INVENTION

The invention relates to a semiconductor device for generating an electron beam having a cathode comprising a semiconductor body having a p-n junction between a semiconductor surface-adjoining n-type region and a p-type region; electrons are generated in the semiconductor body by avalanche multiplication by applying a voltage in the reverse direction across the p-n junction and then these electrons emanate from the semi-conductor body.

The invention relates in addition to a method of manufacturing such a semiconductor device, as well as a camera tube and a display device having such a semiconductor device.

Semiconductor devices of the above-mentioned kind are used, for example, in cathode-ray tubes in which they replace the conventional thermal cathode in which electron emission is generated by heating. In addition to the high energy consumption due to the heating, thermal cathodes have the disadvantage that they are not immediately ready for operation because they first have to be heated before emission occurs. In addition the cathode material is lost over time due to evaporation so that these cathodes have restricted lifetimes.

In order to do away with the need for the heating source, which is cumbersome in practice, and also to remedy the other disadvantages, research has been done into producing a cold cathode.

One of the solutions was considered to be the so-called field emission cathode in which electrons were drawn from a punctiform nonheated cathode by means of a strong external electric field. However, application of this field emission cathode is very restricted due to the required very strong external electric field, the vulnerability of the cathode as a result of electric discharges in the emission space and the ultra-high vacuum (10 to 100 nano-Pascals) necessary for stable emission.

Another solution consists of so-called "negative electron affinity" cathodes in which a semiconductor body of the n-type is covered with a very thin p-type surface region and the p-n junction thus obtained is biased in the forward direction. Since the p-type surface region has a thickness which is smaller than the diffusion-recombination length of the electrons in the p-type region, electrons emitted by the p-n junction in the p-type region, provided they have sufficient energy, can emanate from the semiconductor surface at the surface of the p-type region. In order to stimulate the emanation of the electrons, the surface is usually covered with an electron work function-reducing material, for example, a cesium-containing material.

One of the problems in these "negative electron affinity" cathodes is the occurrence of recombination in the thin p-layer which restricts the injection current. Moreover, during use, the coating layer of electron work function-reducing material is slowly lost, which imposes a restriction on the life of the cathodes.

In addition to the above-mentioned cathodes, there exist cathodes which are based on the emanation of electrons from the semiconductor body when a p-n junction is operated in the reverse direction in such manner that avalanche multiplication occurs. Some electrons may obtain enough kinetic energy to exceed the electron work function potential. These electrons are then liberated at the surface and thus produce an electron beam current. Such a cathode is disclosed in British Pat. No. 1,303,659 and forms the subject matter of the present patent application. In the embodiment of the above-mentioned patent specification a cathode is described in which silicon carbide is used as a semiconductor material. In fact, only with silicon carbide in such a device is such an efficiency obtained, that is to say such a ratio between the generated electron current and the required avalanche current through the p-n junction, that the device is useful for practical application.

When the above-mentioned kinds of cathodes are used, for example, in camera tubes or small display tubes, the released electrons are accelerated by means of control grids and the electron beam thus obtained is often concentrated at a point by means of electron optics. This point, a so-called "cross-over", serves as a real source for the actual electron beam which is then deflected, for example by electromagnetic means such as deflection coils, to scan in a camera tube a photoconductive layer which contains image information.

At the area of the above-mentioned "cross-over" mutual interactions take place between the released electrons. The distribution of the electron energy is altered so that the associated electron temperature is increased and the energy distribution of the electrons becomes larger. This has a detrimental influence on the so-called acceptance curve of the beam in the sense that after-effects occur in the camera tube.

The device described in British Pat. No. 1,303,659 shows a p-n junction which intersects the surface of the device. When the semiconductor device is incorporated in a cathode-ray tube or another discharge device, the cathode will generally form part of a larger assembly in which, as a result of other electrodes, for example an anode or control grids, the generated electrons are drawn away in a direction perpendicular to the major surface of the semiconductor device. Considered in a broader sense the electrons are thus subjected to an electric field having a component perpendicular to the major surface. Major surface is to be understood to mean herein the semiconductor surface including grooves or recesses, if any.

The electric field of the p-n junction emitting electrons as a result of avalanche breakdown is directed perpendicular to the p-n junction. As a result of this, the emanated electrons may have a velocity component in a direction other than the desired direction. This may be disadvantageous, in particular when a narrow electron beam is required.

Furthermore, experiments have demonstrated that in devices of the type described in the British patent specification in which the depletion zone associated with the p-n junction adjoins the surface the electrons generated by means of such a cold cathode have an energy distribution which is not optimum, notably for use in a camera tube. The released electrons as a matter of fact have no sharply defined electron temperature but the energy distribution of the emitted electrons shows a second wide distribution of energy values in addition to a sharp peak which depends on the current through the p-n junction and the voltage on the accelerating electrode. Such an energy distribution detrimentally influences the above-mentioned acceptance curve of the beam.

The form of the energy distribution can presumably be explained as being made up of two distributions. The wide distribution is due to the emanation of electrons which obtain sufficient energy in the depletion region to exceed the electron work function potential and hence emanate from different points on the surface with different potentials. The narrow peak on the other hand occurs mainly by the emanation of electrons which have traversed the whole depletion zone and emanate from the conductive part of the n-type zone which has a substantially constant potential at the surface.

SUMMARY OF THE INVENTION

One of the objects of the invention is to provide a semiconductor device in which the efficiency is so much improved with respect to that of the device described in the British patent specification that silicon may also be used as a material for such a cathode. Another object of the invention is to provide a semiconductor device in which the energy distribution of the electrons in the generated beam has only a narrow spreading.

The invention is, inter alia, based on the discovery of the fact that these objects can be achieved by influencing the electric field in the direct proximity of the p-n junction. According to the invention, the energy distribution of the electrons can be influenced by providing the p-n junction in a suitable manner.

For that purpose, a semiconductor device according to the invention has a surface which has an electrically insulating layer in which at least one aperture is provided. At least one accelerating electrode is provided on the insulating layer at the edge of the aperture. A p-n junction extends substantially parallel to the semiconductor surface at least within the aperture and within the aperture has a lower breakdown voltage than at the remaining parts of the p-n junction. The part of the p-n junction having the lower breakdown voltage is separated from the surface of the device by an n-type conductive layer having such a thickness and doping that at the breakdown voltage and depletion zone of the p-n junction does not extend up to the surface but remains separated therefrom by a surface layer which is sufficiently thin to pass the generated electrons.

The efficiency in such a semiconductor device proves to have been improved so much that even when materials other than silicon carbide are used, for example silicon, efficiencies can be achieved which are useful for practical purposes. This is advantageous because, on the one hand, the cathode structure can be manufactured by means of the technology known for the manufacture of integrated circuits from silicon and, on the other hand, the cathode structures can be incorporated in integrated circuits without major technological problems. A further advantage is that the emission can be modulated by means of voltages on the accelerating electrode. Moreover the direction of the emission can be influenced, if the accelerating electrode consists of two or more parts which are each brought to a different potential. In particular, an emission pattern generated by an annular aperture can be displayed at one point, for example at a point of the photoconductive layer of a camera tube so as to read the picture information present.

In particular, the electrons may also originate from a virtual source, after which this source may be displated at a point on a target by means of known electron optics. An advantage hereof is that dynamic focusing is possible in a simple manner. With the aid of conventional deflection means, the point can be displaced over the surface of the photoconductive layer. In this manner the picture information can be scanned.

Since the electron beam is now incident on the photoconductive layer directly from the cathode without the formation of a "cross-over", it is possible to manufacture a shorter camera tube. By omitting the "cross-over" the electron temperature in the beam is not unnecessarily increased. As compared with a thermal cathode, the tube can also be shortened by the possibility of a virtual electron source in that the virtual source, which has a function comparable to the "cross-over" in tubes having a thermal cathode, would not be present between the target and the cathode but the cathode would be present between the virtual source and the target.

The established efficiency improvement can be explained as follows. First of all, as a result of the strong electric field near the surface which is generated via the accelerating electrode, a decrease of the work function (Schottky effect) is produced. In addition, the formation of space charge is prevented.

Finally, the electron paths are better defined than in existing devices, while in addition the energy distribution of the electrons shows a smaller spreading. By giving the accelerating electrode a sufficiently high potential, the electrons are accelerated in the direction of the electrode. The electrons' velocity components with directions other than the desired directions are drastically reduced with respect to the known device where the p-n junction intersects the surface.

The fact that the p-n junction extends parallel to the semiconductor surface additionally has a favorable influence on the energy distribution of the emitted electrons.

Since in a device according to the invention the depletion zone does not terminate at the surface, the "wide peak" in the energy distribution of the electrons emitted by such a device is not produced.

It is to be noted that in the article "Hot Electron Emission From Shallow p-n Junctions in Silicon" by D. J. Bartelink, J. L. Moll and N. I. Meyer, (Physical Review, Vol. 130, No. 3, May 1, 1963, pp, 972-985) measured results are shown of the energy distribution of electrons which are generated by a reverse p-n junction parallel to the surface by avalanche multiplication and emanate from a silicon body. The measured results shown in the article demonstrate an energy distribution which extends over a much wider area than in the measurements of semiconductor devices according to the invention (the measured energy distributions have half life widths of approximately 1.4 eV and approximately 0.5 eV, respectively, corresponding to electron temperatures of 0.5 eV and 0.2 eV, respectively). This article does not mention a possible contribution of electrons emanating from the depletion zone.

However, in the set-up used there is no mention of an accelerating electrode; nor has the p-n junction locally a lower breakdown voltage.

The breakdown voltage can be locally reduced in various manners. For example, grid damages can be provided in the desired place(s), for example, by bombarding with accelerated particles such as protons. At the area of the aperture a V-groove or pit may also be provided in the semiconductor body so that concentration of the field lines and consequently a lower breakdown voltage occurs.

Preferably, however, the reduction of the breakdown voltage is obtained by an extra doping step. A preferred embodiment of the semiconductor device of the invention is for that purpose characterized in that the breakdown voltage is locally reduced by a locally more highly doped zone of the p-type region, which zone extends into the depletion zone at least during operation.

At the location of the more highly doped p-region a narrowing of the depletion zone occurs and hence a reduction of the breakdown voltage.

Another preferred embodiment in accordance with the invention is characterized in that the width of the more highly doped p-type region is at most 5 microns (micrometers). By this measure excessive current density is not produced.

For the above mentioned use in camera tubes the cathode is preferably constructed with its aperture as a substantially annular slot in which the accelerating electrode is built up from two or more subelectrodes, one subelectrode being situated within the annular slot and one subelectrode being situated outside the annular slot.

The annular slot need not always be circular but may alternatively be, for example, ellipsoidal and in certain circumstances even square or rectangular.

Nor need the aperture always be constructed as a slot. Notably is display applications, circular and also square or rectangular apertures are very suitable.

The invention further relates to a method of manufacturing a semiconductor device as mentioned above. Such a method is characterized in that the starting material is a semiconductor body having a surface-adjoining n-type region forming a p-n junction with a p-type region adjoining same. The surface is covered with an insulating layer and the insulating layer is covered with an electrically conductive layer which is then covered with a masking layer. An aperture is provided in the masking layer after which, via the aperture, the conductive layer and the insulating layer are successively removed by etching. At least the aperture etched in the conductive layer is larger than an underlying surface part within which the p-type region adjoins the surface. While using the masking layer or the masking layer together with the insulating layer as a mask, acceptor atoms are then introduced in the surface part to form a p-type zone which is situated within the surface part and has a higher doping concentration than the p-type region. The masking layer is then removed and while using the conductive layer as a mask, donor atoms are introduced into the surface part down to a depth which is smaller than that of the p-type zone. The conductive layer, serving as an accelerating electrode, the n-type region, and the p-type region are then provided with connection conductors. The advantage of such a method is that in certain steps the insulating layer or the conductive layer serves as a mask and as a result of this the method is partly self-aligning.

A method which is fully self-aligning is characterized in that the n-type region initially extends through the area of the etched aperture. After etching the insulating layer, while using the conductive layer as an etching mask, the n-type region is etched away through its entire depth at the area of the surface part. The p-type zone is then implanted while using the insulating layer as a mask.

The donor ions are preferably implanted in the surface part, via an oxide layer, having such an energy that the maximum donor concentration coincides substantially with the surface of the semiconductor body. As a result of this a series resistance which is as small as possible is obtained in the n-type region.

As described, a cathode according to the invention may advantageously be used in a camera tube or a display device. For example, in a display tube comprising a fluorescent screen which is activated by an electron current, the current may originate from a semiconductor device according to the invention.

BRIEF DESCRIPTION OF THE DRAWINGS

The invention will now be described in greater detail with reference to a few embodiments and the drawing.

DESCRIPTION OF THE PREFERRED EMBODIMENTS

The Figures are diagrammatical and not drawn to scale. For clarity, the thicknesses are strongly exaggerated in the cross-sectional views. Semiconductor zones of the same conductivity type are generally shaded in the same direction. In the Figures corresponding components are generally referred to by the same reference numerals.

Figure 1:
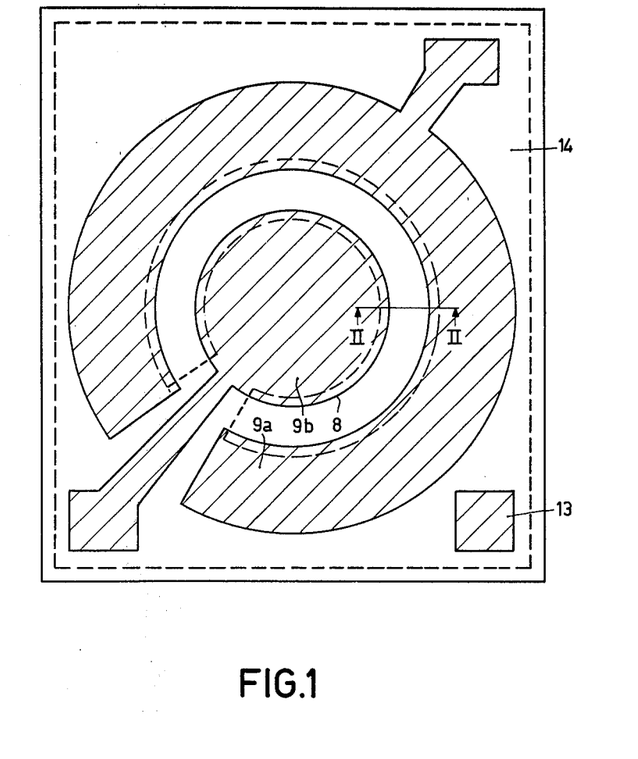
FIG. 1 is a diagrammatic plan view of a semiconductor device according to the invention.
Figure 2:
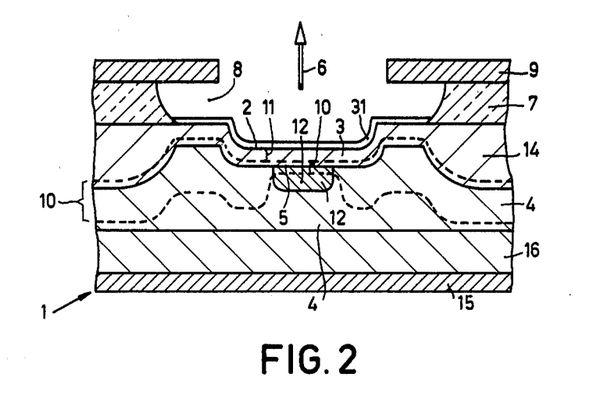
FIG. 2 is a diagrammatic cross-sectional view of the semiconductor device taken on line II—II of FIG. 1.

FIG. 1 is a plan view and FIG. 2 is a cross-sectional view taken on the line II—II of FIG. 1 of a semiconductor device which is designed to generate an electron beam. For this purpose it comprises a cathode having a semiconductor body in this example comprises an n-type region 3 which adjoins a surface 2 of the semiconductor body and forms the p-n junction 5 with a p-type region 4. By applying a voltage in the reverse direction across the p-n junction, electrons are generated by avalanche multiplication which emanate from the semiconductor body. This is shown by means of the arrow 6 in FIG. 2.

In practice the efficiency of such a type of device, notably when silicon is used as a semiconductor material, is so low that no useful cathode is obtained. This can be mitigated by the use of silicon carbide but technologically this is disadvantageous because the technology used in the manufacture of integrated circuits is not suitable for this purpose.

According to the invention, the surface 2 is provided with an electrically insulating layer 7 of, for example, silicon oxide in which at least one aperture 8 is provided. Within the aperture 8 the p-n junction 5 extends substantially parallel to the surface 2. Furthermore, an accelerating electrode 9, in this example of polycrystalline silicon, is provided on the insulating layer 7 on the edge of the aperture 8.

According to the invention, the p-n junction 5 within the aperture 8 locally has a lower breakdown voltage than the remaining part of the p-n junction. In this example the local reduction of the breakdown voltage is obtained in that the depletion zone 10 within the aperture 8 is narrower at the breakdown voltage than at other points of the p-n junction 5. The part of the p-n junction 5 with reduced breakdown voltage is separated from the surface 2 by the n-type layer 3. This layer has such a thickness and doping that at the breakdown voltage the depletion zone 10 of the p-n junction 5 does not extend up to the surface 2. As a result of this a surface layer 11 remains which ensures the conduction of the nonemitted part of the avalanche current. The surface layer 11 is sufficiently thin to pass a part of the electrons generated by avalanche multiplication, which electrons emanate from the semiconductor body 1 and constitute the beam 6.

The reduction in area of the depletion zone 10 and hence the local reduction of the breakdown voltage of the p-n junction 5 is obtained in the present example by providing a more highly doped p-type region 12 within the aperture 8 which forms a p-n junction with the n-type region 3.

The semiconductor device further comprises a connection electrode 13 which, via a contact hole, is connected to the n-type contact zone 14 which is connected to the n-type zone 3. In this example the p-type zone is contacted on its lower side by means of the metallization layer 15. This contacting preferably takes place via a highly doped p-type contact zone 16.

In the example of FIGS. 1 and 2 the donor concentration in the n-type region 3 at the surface is, for example, $5 \cdot 10^{18}$ atoms/cm$^3$, while the acceptor concentration in the p-type region 4 is much lower, for example $10^{15}$ atoms/cm$^3$. The more highly doped p-type region 12 within the aperture 8 at the area of the p-n junction has an acceptor concentration of, for example, $3 \cdot 10^{17}$ atoms/cm$^3$. As a result of this, the depletion zone 10 of the p-n junction 5 at the area of the region 12 is restricted in area, which results in a reduced breakdown voltage. As a result of this, avalanche multiplication will occur first at this location.

In this example the thickness of the n-type region 3 is 0.02 microns. At the donor concentration, sufficient donors can be ionized to reach the field strength (approximately $6 \cdot 10^5$ V/cm) at which avalanche multiplication starts to occur, while nevertheless a minimized surface layer 11 remains. As a result of this, conduction to the p-n junction 5 can take place, while the layer 11 is sufficiently thin to pass a part of the generated electrons. With a thickness of 0.2 microns, the n-type conductive layer will generally exert such an inhibiting influence on the generated electrons that the efficiency of the cathode is too low to be useful.

Upon applying a voltage in the reverse direction across the p-n junction 5 in the device shown in FIGS. 1 and 2, a depletion zone will be formed on either side of the junction. A depletion zone is a region within which substantially no mobile charge carriers are present. Outside the depletion zone the conductivity is high so that substantially the entire voltage is across the depletion zone. The associated electric field can now become so high that avalanche multiplication occurs. Electrons are released which are accelerated by the field present in such manner that upon collision with silicon atoms they form electron-hole pairs. The resulting electrons in turn are accelerated again by the electric field and can again form electron-hole pairs. The energy of the electrons can be so high that the electrons have sufficient energy to emanate from the material. As a result of this an electron current arises which in FIG. 2 is shown diagrammatically by the arrow 6.

By providing, according to the invention, an accelerating electrode 9 which is present on an insulating layer 7 at the edge of an aperture 8, the released electrons can be accelerated in a direction approximately normal to the surface 2 by giving the accelerating electrode 9 a positive potential. An extra acceleration is usually desired in this direction because such a semiconductor structure (cathode) in practice forms part of a device in which, whether or not at some distance, a positive anode or other electrode, for example a control grid, is present.

In this example electron emission takes place from a substantially annular slot. Although, due to the diagrammatic character of the drawing, this is not very apparent, the interruption of the slot for the connection 9b will be very small with respect to the overall circumference so that this interruption is no objection for practical applications. In this case the accelerating electrode consists of two parts 9a and 9b. By giving these parts different potentials, the emanating beam may be caused to diverge or converge and land, for example, on the sensitive part of a target in a camera tube.

In this example the aperture 8 has the shape of a small slot having a width which is of the same order of magnitude as the thickness of the insulating layer 7. For example, the width of the slot is 4 microns and the thickness of the oxide layer is 1 micron. By so choosing these dimensions and arranging the accelerating electrode 9 in the immediate proximity of and preferably around the aperture, an equipotential plane is formed above the slot, which accelerates the electrons.

The electrically insulating layer 7 in this example consists of silicon oxide, while the accelerating electrode 9 and the electrode 13 consist of polycrystalline silicon. For the insulating layer, however, any other suitable material may be chosen, for example, a double layer of silicon nitride-silicon oxide, while for the electrodes any other material conventially used in semiconductor technology may be used, for example aluminium.

The width of the p-type region 12 in this example is 3 microns. This width is preferably less than 5 microns, because otherwise the current density may be excessive along the edge of the region.

As a result of a voltage at the accelerating electrode, reduction of the electron work potential occurs (Schottky effect), which increases the above-mentioned emission. Moreover, the emission of electrons may be further increased by coating the semiconductor surface 2 within the aperture 8 with a work function-reducing material, for example, with a layer 31 of a material containing barium or cesium.

Figure 3:
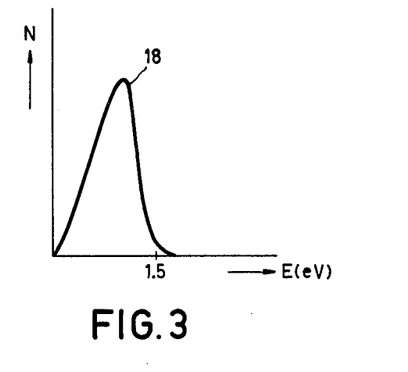
FIG. 3 illustrates the energy distribution of the electrons generated by a semiconductor device according to the invention.

FIG. 3 shows the electron energy distribution as measured from a cathode shown in FIG. 1.

The number of electrons leaving the semiconductor body at a given energy is plotted as a function of that energy. Along the horizontal axis the energy E is plotted in eV, while along the vertical axis the number of emitted electrons N in arbitrary units is plotted. The absolute value of N also depends on the avalanche current and the voltage at the accelerating electrode.

Since according to the invention the p-n junction 40 extends substantially parallel to the surface and the depletion zone 10 does not penetrate to the surface 2, the only electrons which are liberated are those which have traversed the entire depletion zone. The associated energy distribution shows a narrow peak 18. Such an energy distribution is notably very favorable for the use of the cathode in camera tubes.

Figure 4:
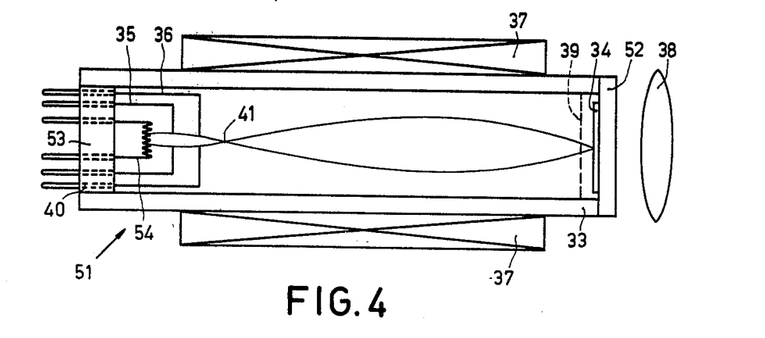
FIG. 4 shows diagrammatically a conventional cathode ray tube.

FIG. 4 shows diagrammatically a camera tube 51, for example, a television camera tube of the conventional type having, for example, a thermal cathode 54. The camera tube further comprises in a hermetically sealed vacuum tube 33, a photoconductive target 34, for example of antimony trisulphide, which layer is scanned by an electron beam, and a screen grid 39.

The camera tube also comprises in the usual manner electrodes 35, 36 to accelerate electrons and focus the electron beam. Furthermore, conventional means are present to deflect the electron beam, so that the target 34 can be scanned. These means consist, for example, of a system of coils 37. A scene to be picked up is projected on the target 34 by means of the lens 38, the end wall 52 being permeable to the incident radiation.

The other end wall 53 has lead throughs 40 for electric connections.

The electrons released from the cathode 54 are first focussed at the point 41 by means of the electrodes 35, 36, which point is then displayed on the photoconductive layer 34 by means of the system of coils 37. Upon focusing the electrons at the point 41 (the cross-over) a mutual interaction between the electrons occurs as a result of which a wider energy spectrum is produced. The wider energy spectrum produces undesirable after-effects.

Figure 5:
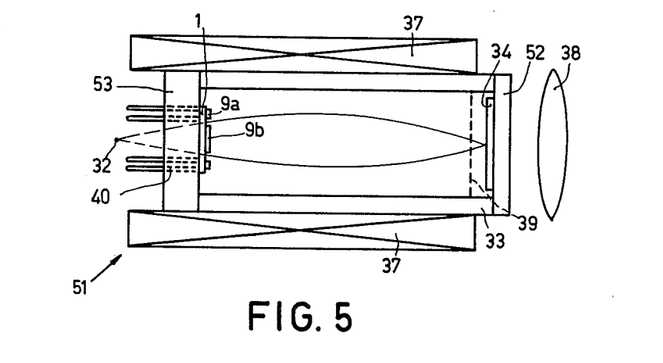
FIG. 5 shows diagrammatically a cathode ray tube in which a semiconductor device according to the invention is used.

FIG. 5 shows diagrammatically a camera tube 51 having a semiconductor cathode 1 according to the invention. The camera tube further comprises in a hermetically sealed vacuum tube 33 a photoconductive target 34, which layer is scanned by the electron beam 6, a system of coils 37 to deflect the beam, and a screen grid 39. A scene to be picked up is projected on the target 34 by means of the lens 38, the end wall 52 being permeable to the incident radiation. For electric connection, the end wall 53 has lead-throughs 40. In this example the semiconductor cathode shown in FIGS. 1 and 2 is mounted on the end wall 53 of the camera tube 51.

Since the cathode emits electrons having a very narrow spread in energy, such a cathode is very suitable for use in such a camera tube (or in a short display tube). This is in contrast with, for example, semiconductor electrodes in which the depletion zone of the emitting p-n junction is exposed at the surface, which semiconductor electrodes emit electrons with a large spread in energy. Since the electrons are not first concentrated in a so-called "cross-over", the energy distribution remains narrow.

By giving the subelectrode 9a a higher positive voltage than the subelectrode 9b, the electrons 6 in this example leave the cathode along a truncated cone surface, in which the electrons appear to originate from the virtual source 32. This makes a shorter camera tube 51 possible. Dynamic focusing is possible by varying the location of the virtual source 32, depending on the location on the target 34 to be scanned. This can be done by varying the voltages at the subelectrodes 9a and 9b.

The fact that the electrons now leave the cathode along a (truncated) cone surface and consequently move along the surface of the beam, moreover has electron-optical advantages with respect to the conventional camera tube shown in FIG. 4 in which the electrons move over the whole cross-section of the beam. The coils 37 influence the electrons which move along the axis of the beam in a different manner than they influence the electrons which move along the surface of the beam.

Focusing on the photosensitive target 34 is also possible by direct control of the cathode. As a result of this, focusing electrodes are not necessary. This means that in a cathode according to the invention the energy spectrum is not widened at a focusing point (cross-over) while fewer auxiliary electrodes in the cathode ray tube and a shorter tube will suffice.

Figure 6:
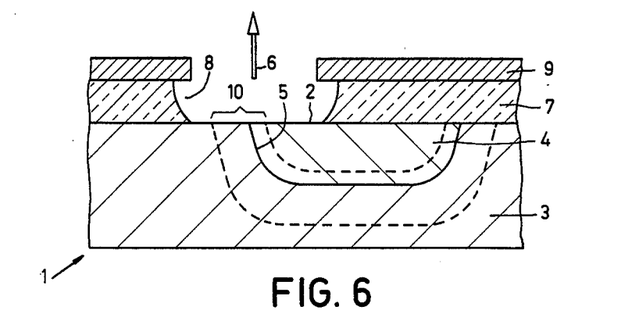
FIG. 6 is a diagrammatical cross-sectional view of a conventional semiconductor device which is provided with an accelerating electrode for comparative measurements.

FIG. 6 shows a semiconductor device 1 having a cathode in which the depletion zone extends up to the surface 2, as is the case, for example, in British Pat. No. 1,303,659. The p-n junction is formed here between an n-type substrate 3 and a p-type region 4 which are provided with contacts (not shown) so as to bias the p-n junction 5 in the reverse direction. As a result of this avalanche multiplication is generated at the p-n junction 5, in which electrons can emanate from the semiconductor body, as indicated by the arrow 6. The emanated electrons in such a device can also be accelerated by means of an accelerating electrode 9 which is provided on the edge of an aperture 8 in the insulating layer 7, which aperture exposes the surface 2. This surface, which, if desired, may be provided with a layer of a work function-reducing material (not shown), is adjoined in this example by the p-n junction 5 and also the depletion zone 10.

Figure 7:
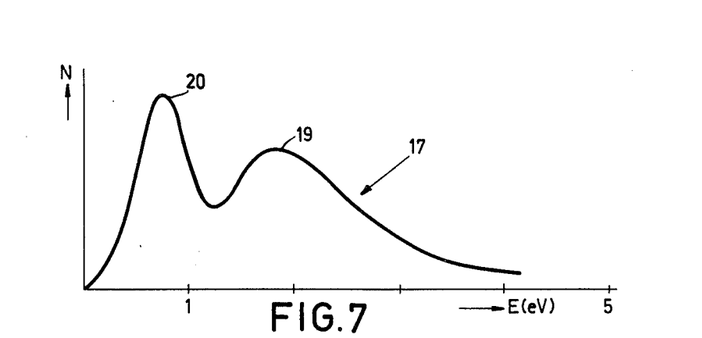
FIG. 7 illustrates qualitatively the energy distribution of the electrons generated by a semiconductor device shown in FIG. 6.

The energy distribution of the electrons emanating from the semiconductor body as a function of the energy E in this case does not have the shape of a narrow band. Measurements at a cathode as shown in FIG. 6 in which the depletion zone 10 comes to the surface 2, have revealed that the energy distribution can be represented by the curve 17 in FIG. 7. Besides a sharp peak 20 which depends on the current through the p-n junction and the voltage at the accelerating electrode, the energy distribution shows a wide band 19. A possible explanation for this is that a number of electrons obtain sufficient energy to emanate before they have traversed the entire depletion zone. As a result of this these electrons are liberated at different locations at the surface 2 within the depletion zone 10. Because substantially the entire reverse voltage is across the depletion zone, a voltage gradient occurs along the surface 2. Electrons which emanate, consequently leave the surface 2 at different starting potentials and hence obtain different energies. The narrow peak 20 according to this explanation is formed by electrons which have traversed the depletion zone 10 entirely or substantially entirely and leave having as a starting potential the potential of the n region.

Figure 8:
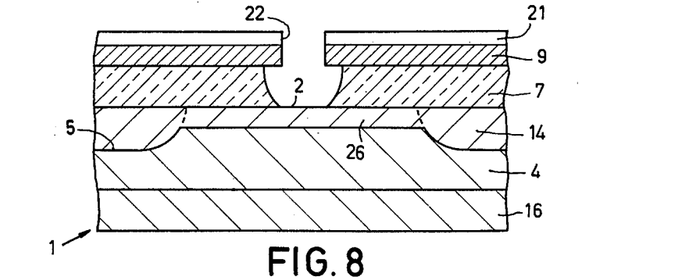
FIGS. 8 to 10 are diagrammatic cross-sectional views of successive stages in the production of the semiconductor device shown in FIG. 2 illustrating a method according to the invention.
Figure 9:
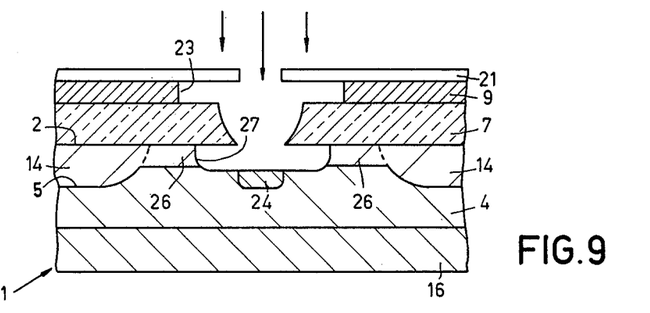
Figure 10:
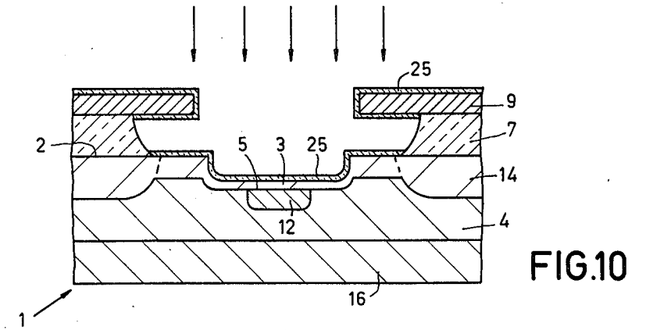

The device shown in FIGS. 1 and 2 can be manufactured as follows (FIGS. 8 to 10).

The starting material is a semiconductor body 1 of silicon having an n-type region (14, 26) which adjoins a surface 2 and which forms a p-n junction 5 with an adjoining p-type region 4. This semiconductor body may be obtained, for example, as follows. An epitaxial layer 4 having a thickness of 10 microns and a resistivity of 10 ohm.cm is provided by means of epitaxial growth on a p-type silicon substrate 16 having in this example a resistivity of 0.001 ohm.cm. The n-type contact zone 14 is then provided by diffusion of, for example, phosphorus in the semiconductor body down to a depth of approximately 2 microns. The surface concentration of the zone 14 is, for example $10^{19}$ donor atoms/cm$^3$. The n-type surface zone 26 is provided down to a smaller depth than the contact zone 14, for example, by means of an arsenic implantation. Arsenic ions are implanted with an energy of approximately 50 kV and a dose of approximately $10^{14}$ ions/cm$^2$ down to a depth of, for example 0.2 microns.

The surface 2 is then covered in known manner by an insulating layer 7 such as silicon oxide, for example by thermal oxidation. An electrically conductive layer 9, for example, a layer of polycrystalline silicon, is then provided on the layer 7 which has a thickness of, for example, 1 micron. This layer 9 is then covered with a masking layer 21 of, for example, silicon nitride.

An aperture 22 is defined in the masking layer by means of photolithographic etching methods, after which via the aperture first an aperture is etched in the conductive layer 9 of the polycrystalline silicon, for example by means of plasma etching, and then an aperture is etched in the insulating layer 7, for example, by means of a solution of hydrofluoric acid and ammonium fluoride in water. The configuration shown in FIG. 8 is then obtained.

Referring to FIG. 9, the aperture in the polycrystalline silicon 9 is then expanded, by means of undercutting, up to the edge 23. The aperture bounded by the edge 23 thus becomes larger than the part of the surface 2 exposed by the etching of the insulating layer 7. The etchant used for undercutting (for example a mixture of hydrofluoric acid, nitric acid, and acetic acid) simultaneously attacks the n-type surface zone 26. The etching treatment is continued until the surface zone 26 is removed throughout its thickness at the area of the aperture 22. Since the etchant used attacks the polycrystalline silicon also more rapidly in a lateral direction than the monocrystalline silicon, the aperture in the layer 9 of the polycrystalline silicon is larger than the aperture 27 in the monocrystalline silicon. Boron ions, for example, are then implanted with an energy of 20 kV and a dose of $8 \cdot 10^{12}$ ions/cm$^2$, the masking layer 21 in combination with the insulating layer 7 serving as an implantation mask. After the implantation the boron is further diffused, if necessary, which results in the p-type region 24 which has an increased doping (a surface doping concentration of $10^{17}$ to $10^{18}$ acceptor atoms/cm$^3$) with respect to the epitaxial layer 4. The device shown in FIG. 9 is then obtained.

After removing the masking layer 21, the oxide layer 7 is etched in a solution of hydrofluoric acid and ammonium fluoride in water with the layer 9 of polycrystalline silicon as an etching mask. The exposed monocrystalline silicon surface as well as the polycrystalline silicon are then provided with an oxide skin 25 having a thickness of approximately 0.02 microns, for example by thermal oxidation. The oxide skin, in addition to protecting the silicon surfaces during a subsequent implantation of donors, also serves to influence the implantation in such manner that after the implantation and a subsequent annealing step the maximum concentration of the implanted donors coincides approximately with the surface of the semiconductor body. This gives good electrical conduction along the surface.

Referring to FIG. 10, the donors are provided, for example, by an arsenic implantation down to a depth which is less than that of the p-type region 24, for example 0.02 microns, with an energy of 40 kV and a dose of $3 \cdot 10^{13}$ ions/cm$^2$. The n-type region 3 is formed by this implantation. The doping of the surface zone of the p-type region 24 is thereby reversed; the remaining part of region 24 forms the p-type region 12 shown in FIG. 2. The device shown in FIG. 10 is then obtained.

After the annealing step already mentioned, the oxide skin 25 is removed, for example, by etching. In locations not shown in the cross-sectional view, contact holes are provided in the insulating layer for contacting the n-type zone 14, for example, before providing the conductive layer 9. The conductive layer 9 during the above-mentioned etching of the polycrystalline silicon, is etched in a pattern, the accelerating electrodes 9a, 9b and the connection electrode 13 being obtained.

After providing a metallization layer 15 on the bottom of the device, the device shown in FIGS. 1 and 2 is obtained. Finally, connection conductors are provided on the electrodes 9, 13, and 15. A layer 31 of a work function-reducing material such as barium or cesium may be provided on the surface 2.

Figure 11:
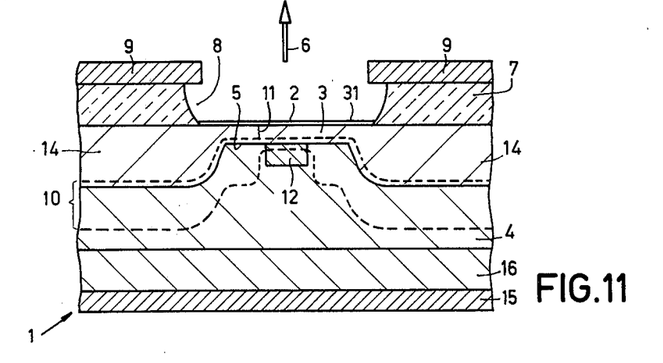
FIG. 11 is a diagrammatic cross-sectional view of another semiconductor device according to the invention.

FIG. 11 is a diagrammatic cross-sectional view of another device according to the invention with the same plan view as FIG. 1. The cross-sectional view is again taken on the line II—II. This device comprises a cathode having a semiconductor body 1, for example of silicon, having a p-n junction 5 between an n-type region 3 adjoining the surface 2 of the semiconductor body 1 and a p-type region 4. By applying a voltage in the reverse direction across the p-n junction, electrons are generated which can emanate from the semiconductor body, which is indicated by the arrow 6.

According to the invention, the surface 2 is provided with an electrically insulating layer 7 of, for example, silicon oxide, in which at least one aperture 8 is provided. Within the aperture 8, the p-n junction 5 extends substantially parallel to the surface 2. Furthermore, an accelerating electrode 9 which in this example is of polycrystalline silicon, is provided on the insulating layer 7 on the edge of the aperture 8.

According to the invention the p-n junction 5 comprises within the aperture 8 locally a lower breakdown voltage than the remaining part of the p-n junction. In this example, the local reduction of the breakdown voltage is obtained in that within the aperture 8 the depletion zone 10 at the breakdown voltage is narrower than at other points of p-n junction 5. The part of the p-n junction 5 having a reduced breakdown voltage is separated from the surface 2 by the n-type layer 3. This layer has such a thickness and doping that, at the breakdown voltage, the depletion zone 10 of the p-n junction 5 does not extend up to the surface 2. As a result of this, a surface layer 11 remains present which ensures the conduction of the avalanche current. The surface layer 11 is sufficiently thin to pass a part of the electrons generated by avalanche multiplication, which electrons emanate from the semiconductor body 1 and form the beam 6.

The reduction in area of the depletion zone 10 and hence the local reduction of the breakdown voltage of the p-n junction 5 is obtained in this case also by providing a more highly doped p-type region 12, within the aperture 8, which forms a p-n junction with the n-type region 3.

The semiconductor device is further provided with a connection electrode 13 which, via a contact hole, is connected to the n-type contact zone 14 which is connected to the n-type zone 3. The p-type zone 4 in this example is contacted on its lower side by means of the metallization layer 15, preferably via a highly doped p-type contact zone 16.

In FIG. 11 embodiment the donor concentration in the n type region 3 is, for example, $5 \cdot 10^{18}$ atoms/cm$^3$, while the acceptor concentration in the p-type region 4 is much lower, for example, $10^{15}$ atoms/cm$^3$.

The more highly doped p-type region 12 within the aperture 8 near the p-n junction has an acceptor concentration of, for example, $2 \cdot 10^{17}$ atoms/cm$^3$. As a result of this, the depletion zone 10 of the p-n junction is reduced in area at the area of this region 12, which results in a reduced breakdown voltage. As a result of this avalanche multiplication will occur first at this location.

The thickness of the n-type region 3 in this example is again 0.02 microns. With the donor concentration, sufficient donors can be ionized to reach the field strength (approximately $6 \cdot 10^5$ V/cm) at which avalanche multiplication starts to occur, while nevertheless a surface layer 11 remains present, so that on the one hand conduction to the p-n junction 5 can take place, while the layer on the other hand is sufficiently thin to pass a part of the generated electrons.

Figure 12:
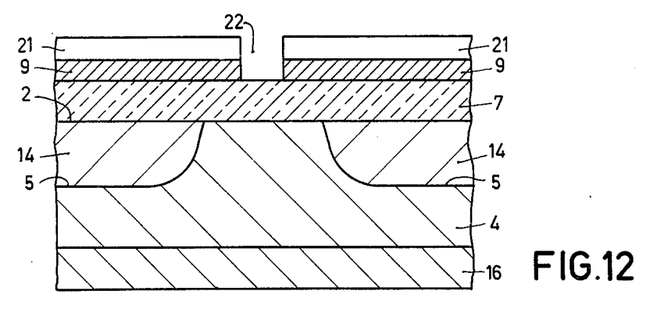
FIGS. 12 to 14 are diagrammatic cross-sectional view of successive stages in the production of the semiconductor device shown in FIG. 11 illustrating a method according to the invention.
Figure 13:
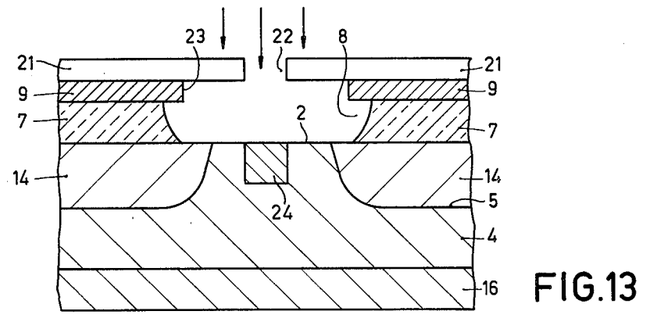
Figure 14:
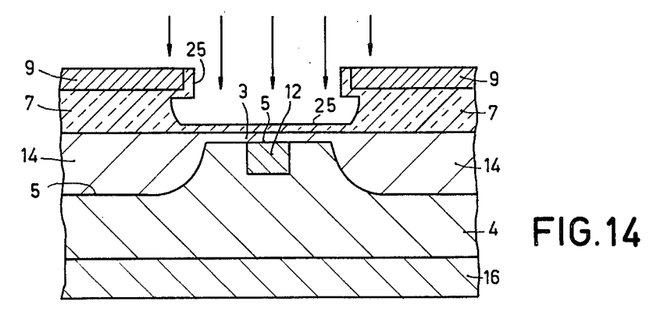

The FIG. 11 device can be manufactured as follows (FIGS. 12 to 14).

The starting material is a semiconductor body 1 having an n-type region 14 which adjoins the surface 2 and which forms a p-n junction 5 with an adjoining p-type region 4. This semiconductor body may be obtained, for example, by growing a p-type epitaxial layer having a thickness of 10 microns and a resistivity of 10 ohm.cm on a p-type silicon subtrate 16 having in this example a resistivity of 0.001 ohm.cm. The n-type region 14 is diffused into the semiconductor body by means of diffusion of, for example, phosphorus, down to a depth of approximately 2 microns. The doping concentration of the n-type region 14 at the surface is, for example $2 \cdot 10^{19}$ atoms/cm$^3$.

The surface 2 is then covered in known manner with an insulating layer 7 such as silicon oxide, for example, by thermal oxidation. An electrically conductive layer 9, for example a layer of polycrystalline silicon, is then provided on the layer 7 having a thickness of, for example, 1 micron. This layer 9 is then covered with a masking layer 21, for example, silicon nitride.

A window 22 for the subsequent etching step is then defined in the masking layer 21 by means of photolithographic etching methods. The window 22 is proportioned so that, in projection, it lies between the parts of the n-type region 14. The underlying layer 9 of polycrystalline silicon is then etched via the window 22, for example, by means of plasma etching. The configuration shown in FIG. 12 is then obtained.

Etching of the polycrystalline silicon is continued until the aperture is larger than the underlying part of the p-type region 4 adjoining the surface 2 which is bounded by the parts of the n-type region 14; in other words, etching is continued until, in projection, the edge 23 of the aperture in the polycrystalline silicon lies above the n-type region 14.

Via the aperture 22, the oxide layer 7 is then etched, for example, by means of a solution of a hydrofluoric acid and ammonium fluoride in water. During this etching, the layer 9 of the polycrystalline silicon serves as a mask, so that ultimately the aperture 8 is obtained. (FIG. 13).

By means of a boron implantation, the region 24 which has an increased acceptor doping as compared with the p-type region 4 is then deposited within the aperture. The implantation energy is chosen to be so low (for example 10 kV with a dose of $10^{13}$ ions/cm$^2$) that the nitride can serve as a mask. After the deposition the boron is further diffused, if desired, which results in a surface concentration of $10^{17}$ to $10^{18}$ atoms/cm$^3$. (FIG. 13).

A light oxidation step is then performed so that both the semiconductor surface and the edges 23 of the aperture in the polycrystalline silicon layer 9 are covered with an oxide skin 25. The oxide skin again has a thickness of approximately 0.02 microns (FIG. 14).

After the masking layer 21 has been removed, an implantation of donors, for example, a shallow arsenic implantation down to a depth of 0.02 microns is carried out, the layer 9 serving as a mask. This implantation is carried out, for example, with an energy of 40 kV and a dose of $3 \cdot 10^{13}$ ions/cm$^2$. Since the implantation is carried out down to a smaller depth than that of the p-type region 24, the doping is partly reversed; the remaining part of region 24 forms the p-type zone 12 shown in FIG. 11. After providing, if desired, a layer 31 of electron work function-reducing material, the semiconductor device shown in FIG. 11 is obtained.

Figure 15:
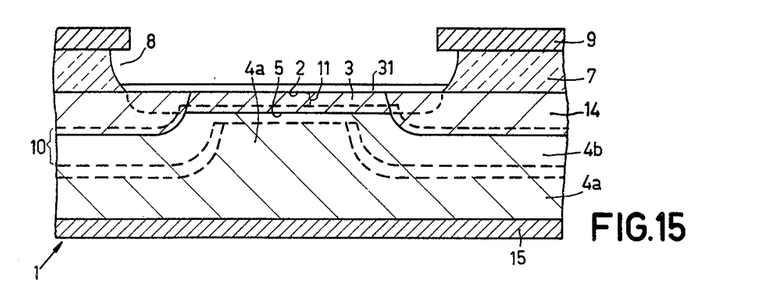
FIG. 15 is a diagrammatic cross-sectional view of another semiconductor device according to the invention.

The local narrowing of the depletion zone and hence a reduced breakdown voltage can also be obtained in quite a different manner. FIG. 15, for example, is a cross-sectional view of a semiconductor device in which the emissive part of the p-n junction is formed between a highly doped n-type region 3 and a p-type region 4 which at the area of the p-n junction comprises a p-type region 4a which is surrounded by a p-type region 4b having a lower acceptor concentration. The junction between the p-type region 4a and the n-type region 3 thus has a lower breakdown voltage and is situated entirely within an aperture 8 in an insulating layer 7. On the insulating layer 7, according to the invention, an accelerating electrode 9 is provided. At the area of the aperture 8 the p-n junction 5 extends substantially parallel to the surface 2, while the n-type region 3 has such a thickness and doping concentration that upon breakdown a conductive surface layer 11 is present. Within the aperture the surface 2 is again provided, if necessary, with a layer 31 of an electron work function-reducing material. The n-type region 4 is again connected, via the n-type zone 14, to a connection electrode while the p-type region 4 can be contacted again on its lower side via a metallization 15.

Figure 16:
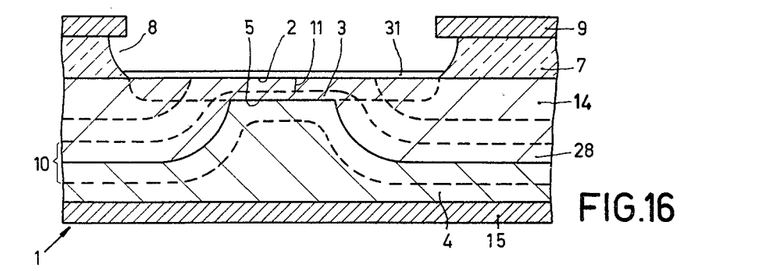
FIG. 16 is a diagrammatic cross-sectional view of still another semiconductor device according to the invention.

FIG. 16 is a cross-sectional view of a device in which the p-n junction 5 extends between a p-type region 4 and an n-type region 3, 28, the n-type region 3 being again a highly doped surface zone, while the region 28 has a much lower doping concentration. The p-n junction 5 extends parallel to the surface 2 in the region where the p-n junction is formed between the p-type region 4 and the highly doped n-type surface zone 3. The n-type surface zone again has such a thickness and doping concentration that conduction along the surface remains possible in the layer 11. Since the donor concentration of the n-type region 3 is much higher than that of the n-type region 28, a narrowing of the depletion zone occurs near the junction between the regions 3 and 4 and hence a reduction of the breakdown voltage. This region again lies within the aperture 8 in the insulating layer 7 which in turn is covered with an accelerating electrode 9.

Figure 17:
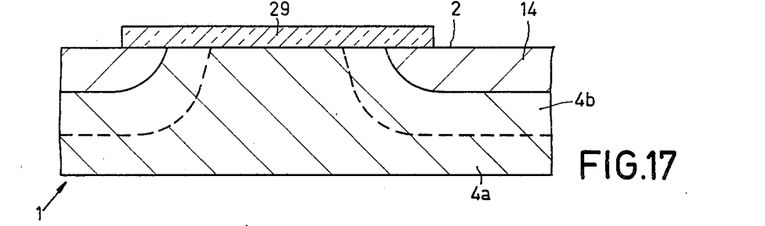
FIG. 17 is a diagrammatic cross-sectional view of the semiconductor device shown in FIG. 15 during one stage of its manufacture.

FIG. 17 is a cross-sectional view of the semiconductor devices shown in FIGS. 15 and 16 during a stage of this manufacture. The device is manufactured, for example, by starting from a p-type semiconductor body 1 having an acceptor concentration of $10^{17}$ to $10^{18}$ atoms/cm$^3$. At the area of the aperture to be provided the surface 2 is provided photolithographically with a mask 29, for example, of silicon oxide. A diffusion step with donors for example phosphorus atoms, is then carried out with such a concentration that in the region 4b the absolute concentration of donor atoms is slightly lower than that of the acceptor atoms, so that here a low-doped p-type region 4b is formed beside the more highly doped region 4a. A diffusion step with, for example, phosphorus atoms is then carried out again down to a smaller depth than the proceding one. As a result of this n-type region 14 having a surface concentration of, for example, $10^{19}$ atoms/cm$^2$ is obtained. The configuration shown in FIG. 17 is obtained.

After removing the oxide mask 29, again an insulating layer 7 and a conductive layer 9, respectively, are provided on the surface 2, in which an aperture 8 is formed by etching. Using the conductive layer 9 or the insulating layer 7 as a mask, a thin n-type layer 3 is provided by means of ion implantation. The implantation is carried out, if desired, through a thin oxide layer.

After providing the surface 2 within the aperture 8 and providing the device with connection electrodes and metallization 15, (and if desired, providing a layer 31 of electron work function-reducing material), the device shown in FIG. 15 is obtained.

When the first phosphorus diffusion step is carried out so that the absolute concentration of phosphorus atoms after diffusion is slightly higher than the acceptor concentration, the device shown in FIG. 16 is obtained with a high-ohmic n-type zone 28 instead of the high-ohmic p-type zone 4b.

Figure 18:
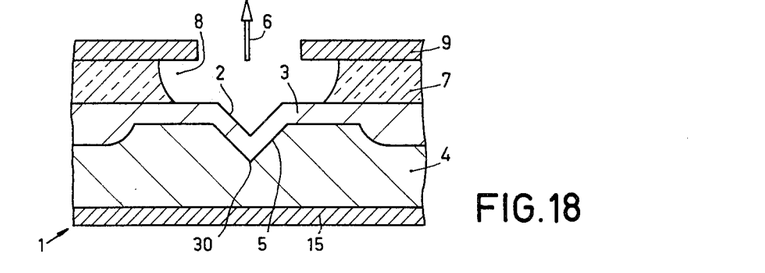
FIG. 18 is a diagrammatic cross-sectional view of still another semiconductor device according to the invention.

FIG. 18 is a cross-sectional view of a semiconductor device according to the invention in which the breakdown voltage of the p-n junction 5 is locally reduced by providing a V-shaped recess in the surface 2. As a result of this shape, the breakdown occurs sooner in the point 30 of the V than elsewhere in the semiconductor body as a result of concentration of electric field lines.

In the camera tube shown in FIG. 5 the conductive layer 34 may be replaced by a fluorescent screen so that the tube may be used for display purposes.

In such applications, a circular, rectangular or ellipsoidal or square aperture may advantageously be used in the insulating layer of the semiconductor device. The circular, rectangular, ellipsoidal or square emission pattern is then displayed on a fluorescent screen in a generally known manner.

Figure 19:
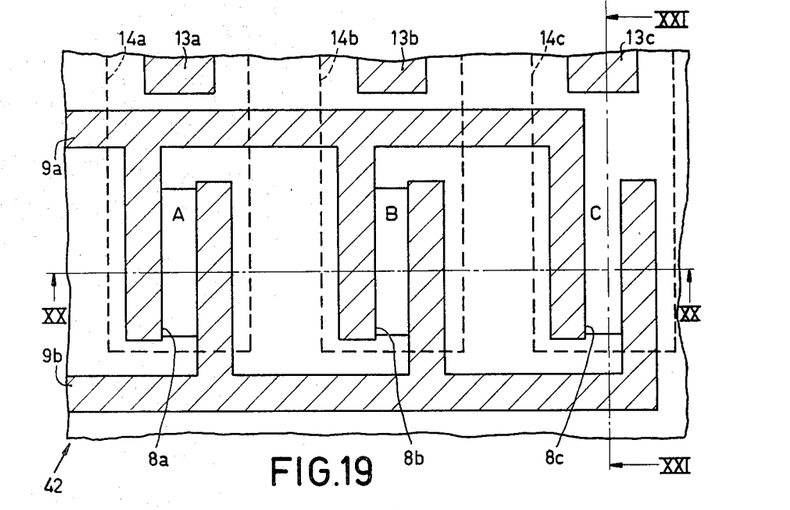
FIG. 19 is a diagrammatic plan view of a semiconductor device according to the invention for application in a display device.
Figure 20:
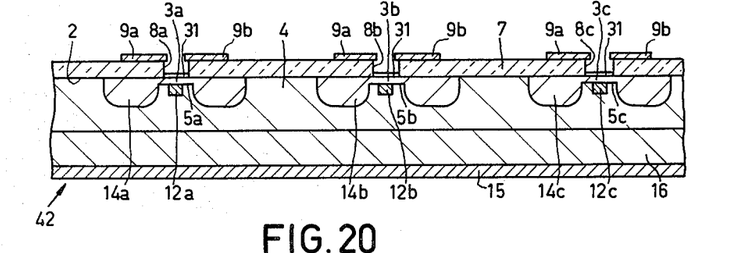
FIG. 20 is a diagrammatic cross-sectional view of the semiconductor device shown in FIG. 19 taken on the line XX—XX.
Figure 21:
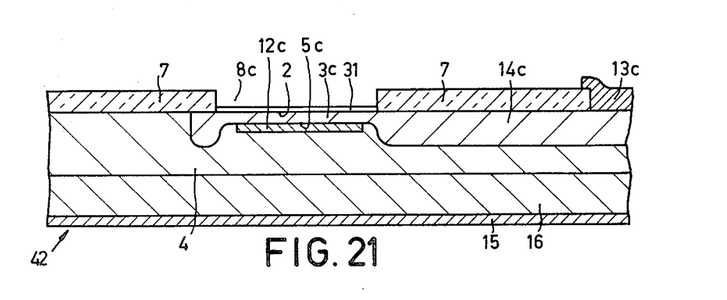
FIG. 21 is a diagrammatic cross-sectional view of the semiconductor device shown in FIG. 19 taken on the line XXI—XXI.

FIG. 19 is a plan view and FIGS. 20 and 21 are cross-sectional views taken on the lines XX—XX and XXI—XXI of a semiconductor device for such an application.

FIG. 19 is a diagrammatic plan view of a silicon slice 42 in which 3 cathodes have been constructed which are denoted by the letters A, B, C.

The avalanche multiplication occurs in three different p-n junctions 5a, 5b, 5c between highly doped n-type regions 3a, 3b, 3c and a common p-type region 4 which for the sake of a reduced breakdown voltage is provided at the area of the cathodes A, B, and C with more highly doped p-regions 12a, 12b, 12c adjoining the respective p-n junctions. The surface 2 is covered with an insulating layer 7 on which accelerating electrodes 9a and 9b are provided around the rectangular apertures 8a, 8b, 8c. The common p-type region is contacted on its lower side by means of the metallization 15 via a low ohmic p-type contact zone 16. The n-type contact zones 14a, 14b and 14c are connected via contact holes with the connection electrodes 13a, 13b, 13c. The accelerating electrodes 9a and 9b are comb-shaped, the teeth of the comb interdigitating in which between two teeth alternately an aperture 8 is situated having a rectangular shape. In the apertures 8a, 8b, 8c the surface 2 is again covered, if desired, with a layer 31 of electron work function-reducing material.

Such a device is very suitable for use in a color display tube in which signals corresponding to the red, green and blue information are applied to the connections 13a, 13b and 13c, respectively. By giving the electrodes 9a and 9b different potentials, the three signals are displayed in three adjacent spots on the fluorescent screen.

A number of the cathodes according to the invention having, for example, a circular aperture, surrounded by an accelerating electrode may also be integrated in an XY matrix in which, for example, the n-type regions are driven by the X-lines and the p-type regions by the Y-lines. By means of control electronics, for example shift registers, the contents of which determine which of the X-lines and the Y-lines, respectively, are driven, a given pattern of cathodes may be caused to emit, while for example, via other registers in combination with digital-to-analog converters, the potential of the accelerating electrodes can be adjusted. Herewith flat display devices can be realized in which in an evacuated space a fluorescent screen is present at a few millimeters from the semiconductor device and is activated by the electron current originating from the semiconductor device.

Figure 22:
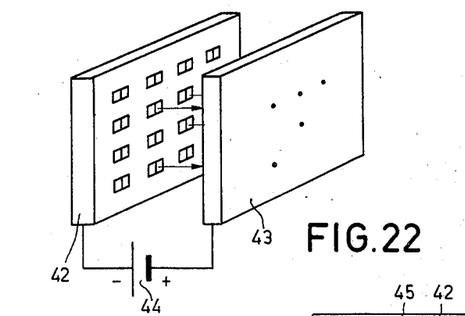
FIG. 22 is a diagrammatic perspective view of a part of a display device in which a semiconductor device according to the invention is used.

FIG. 22 is a diagrammatic perspective elevation of such a flat display device which in addition to the semiconductor device 42 comprises a fluorescent screen 43 which is activated by the electron current originating from the semiconductor device. The distance between the semiconductor device and the fluorescent screen is, for example, 5 mm, while the space in which they are present is evacuated. Between the semiconductor device 42 and the screen 43 a voltage is applied on the order of 5 to 10 kV via the voltage source 44, which produces such a high field strength between the screen and the device that the image of a cathode is of the same order of magnitude as the cathode.

Figure 23:
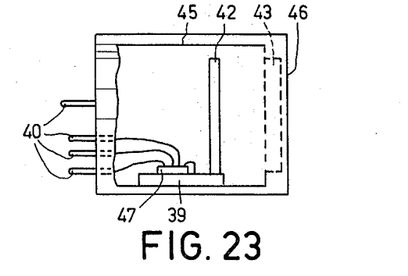
FIG. 23 shows diagrammatically such a display device for display applications.

FIG. 23 shows diagrammatically such a display device in which in an evacuated space 45 the semiconductor device 42 is provided at approximately 5 mm from the fluorescent screen 43 which forms part of the end wall 46 of the space. The device 42 is mounted on a holder 39 on which, if desired, other integrated circuits 47 are provided on behalf of the control electronics. The space 45 is provided with lead-throughs 40 for external connections.

Figure 24:
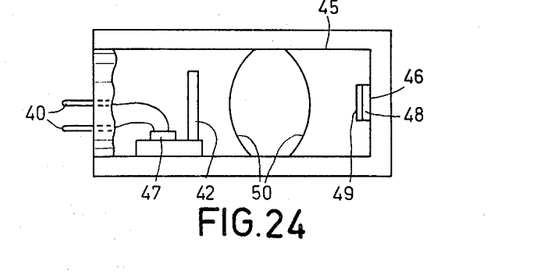
FIG. 24 shows diagrammatically such a display device for use in electron lithography.

FIG. 24 shows diagrammatically such a vacuum space 45. In the space is present a diagrammatically shown system 50 of electron lenses. In the end wall 46 is provided, for example, a silicon slice 48 covered with a photoresist layer 49. The pattern generated in the device 42 is displayed, if desired smaller, on the photoresist layer 49 via the system of lenses.

Such a device enables one to display patterns on a photoresist layer. This presents great advantages because as a result of this the usual photomasks may be omitted and the desired patterns can be generated in a simple manner and corrected, if necessary, via the control electronics.

It will be obvious that the invention is not restricted to the above examples. For example, when the cathode is incorporated in an integrated circuit, the p-type region 4 will not be connected to a connection conductor via a metallization layer on the lower side of the semiconductor body but via a diffused p-type zone. Nor need the p-type region necessarily be an (epitaxial) layer having a uniform doping but this may alternatively be a diffused zone.

As already noted, various shapes are possible, notably in display applications, for the shape of the aperture, for example, circular or square. By dividing the accelerating electrode into, for example, 4 subelectrodes at which different voltages can be set up, the emanating electron beam can be deflected in various directions.

In a configuration as that shown in FIG. 19, the emanating beams can be deflected in nonparallel directions relative to each other by means of a different metallization pattern, if this should be desired. For example, the beams can be made to coincide at one point and be deflected by other means.

Many variations are also possible in the methods of manufacture. Instead of ion implantation, as in the examples described, the regions 12 and 3 may also be provided by a deposition normal to the surface and followed by diffusion. In that case the oxide skin 25 is removed before the deposition or is not provided at all.

We claim:

1. A method of manufacturing a semiconductor device for generating an electron beam by avalanche multiplication across a reverse biased p-n junction, said method comprising the steps of:
providing a semiconductor body having a surface, said body having a surface-adjoining n-type conductivity layer and a p-type conductivity layer adjoining the n-type layer, the n-type layer being disposed between the surface of the semiconductor body and the p-type layer, said p-type and n-type layers forming a p-n junction therebetween;
covering the surface of the semiconductor body with a layer of an electrically insulating material;
covering the layer of electrically insulating material with a layer of electrically conductive material;
covering the layer of electrically conductive material with a layer of masking material;
providing an aperture in the mask layer;
etching apertures into the conductive, insulating, and n-type layers through the aperture in the mask layer, the aperture in the conductive layer being larger than the aperture in the n-type layer;
doping the p-type layer through the apertures with acceptor atoms to form a heavily doped p-type region of higher doping concentration than the p-type layer;
removing the mask layer; and
doping the p-type region through the apertures with donor atoms to form a surface-adjoining n-type region in the heavily doped p-type region.

2. A method as claimed in claim 1, wherein the doping steps comprise ion implanting the dopants.

3. A method as claimed in claim 2, wherein before implanting the donor ions, any exposed semiconductor surfaces are provided with an oxide layer.

4. A method as claimed in claim 3, wherein the energy of the donor ions is selected such that the maximum donor concentration is substantially at the surface of the semiconductor body.

5. A method as claimed in claim 4, wherein after the formation of the heavily doped p-type region and prior to doping the heavily doped p-type region with donor ions, the aperture in the insulating layer is enlarged until it is larger than the aperture in the conductive layer.

* * * * *